US007582674B2

(12) United States Patent
Raederstorff et al.

(10) Patent No.: US 7,582,674 B2
(45) Date of Patent: Sep. 1, 2009

(54) NUTRACEUTICAL COMPOSITIONS AND USE THEREOF

(75) Inventors: Daniel Raederstorff, Brunstatt (FR); Joseph Schwager, Uffheim (FR); Volker Spitzer, Lörrach (DE); Peter Weber, Malsburg-Marzell (DE)

(73) Assignee: DSM IP Assets B.V., TE Heerlen (NL)

( * ) Notice: Subject to any disclaimer, the term of this patent is extended or adjusted under 35 U.S.C. 154(b) by 168 days.

(21) Appl. No.: 10/558,042

(22) PCT Filed: May 18, 2004

(86) PCT No.: PCT/EP2004/005362

§ 371 (c)(1),
(2), (4) Date: Nov. 23, 2005

(87) PCT Pub. No.: WO2004/105517

PCT Pub. Date: Dec. 9, 2004

(65) Prior Publication Data

US 2006/0287256 A1 Dec. 21, 2006

(30) Foreign Application Priority Data

May 27, 2003 (EP) .................................. 03011892

(51) Int. Cl.
*A61K 31/35* (2006.01)
*A61K 31/355* (2006.01)
*A61K 31/05* (2006.01)
(52) U.S. Cl. ........................ 514/456; 514/458; 514/460; 514/731; 514/734
(58) Field of Classification Search ........................ None
See application file for complete search history.

(56) References Cited

U.S. PATENT DOCUMENTS 6,486,203 B1   11/2002   Dannenberg

FOREIGN PATENT DOCUMENTS

| CN | 1 127 070 A | 7/1996 |
|---|---|---|
| GB | 2 317 561 A | 4/1998 |
| WO | WO 95/21542 A1 | 8/1995 |
| WO | WO 97/39746 A1 | 10/1997 |
| WO | WO 99/48386 A1 | 9/1999 |
| WO | WO 99/59561 A2 | 11/1999 |
| WO | WO 99/59561 A3 | 11/1999 |
| WO | WO 00/21507 A3 | 4/2000 |
| WO | WO 01/30336 A2 | 5/2001 |
| WO | WO 01/30336 A3 | 5/2001 |
| WO | WO 01/51088 A1 | 7/2001 |
| WO | WO 01/95727 A1 | 12/2001 |

OTHER PUBLICATIONS

O'Neil et al. (eds.), The Merck Index, An Encyclopedia of Chemicals, Drugs, and Biologicals, 13th Editions, 2001, Merck & Co., Whitehouse Station, NJ, only pp. 623 and 1462 supplied, see entries 3557 (EGCG) and 8243 (resveratrol).*
Yoon et al., "Effect of Selected Phytochemicals and Apple Extracts on NF-(kappa)B Activation in Human Breast Cancer MCF-7 Cells," Journal of Agricultural and Food Chemistry, 55(8), 3167-3173 (2007); web published on Mar. 21, 2007.*
Wu et al., "Inhibition of Prostaglandin E2 Production of a Macrophage Cell Line by Some Phytochemicals," Food Science and Agricultural Chemistry, 3(2), 59-71 (2001); only abstract supplied.*
Lin, Jen-Kun, "Mechanisms of Cancer Chemoprevention by Phytochemicals and Phytophenols," Food Science and Agricultural Chemistry, 2(4), 189-201 (2000); only abstract supplied.*
Wu et al., "Inhibition of Prostaglandin E2 Production of a Macrophage Cell Line by Some Phytochemicals," Food Science and Agricultural Chemistry, 3(2), 59-71 (Jun. 2001).*
Lin, Jen-Kun, "Mechanisms of Cancer Chemoprevention by Phytochemicals and Phytophenols," Food Science and Agricultural Chemistry, 2(4), 189-201 (Oct. 2000).*
DeBandt, M., et al., "Vitamin E Uncouples Joint Destruction and Clinical Inflammation in a Transgenic Mouse Model of Rheumatoid Arthritis," *Arthritis Rheum.*, vol. 46, No. 2, pp. 522-532 (2002).
Barnes, S., et al., "Isoflavonoids and Chronic Disease: Mechanisms of Action," *BioFactors*, 12, pp. 209-215 (2000).
Calder, P.C. and Zurier, R.B., "Polyunsaturated Fatty Acids and Rheumatoid Arthritis," *Curr. Opin. Clin. Nutr. Metab. Care*, 4, pp. 115-121 (2001).
Chandra, V., et al., "First Structural Evidence of a Specific Inhibition of Phospholipase $A_2$ by α-Tocopherol (Vitamin E) and its Implications in Inflammation: Crystal Structure of the Complex Formed Between Phospholipase $A_2$ and α-Tocopherol at 1.8 Å Resolution," *J. Mol. Biol.*, 320, pp. 215-222 (2002).
Eichbaum, F.W., et al., "Anti-Inflammatory Effect of Wayfarin and Vitamin $K_1$," *Naunyn-Schmeidesberg's Arch. Pharmacol.*, 307, pp. 185-190 (1979).
Gentilli, M., et al., "Resveratrol Decreases Hyperalgesia Induced By Carrageenan in the Rat Hind Paw," *Life Sciences*, 68, pp. 1317-1321 (2001).
Gil, Á., "Polyunsaturated Fatty Acids and Inflammatory Diseases," *Biomed. Pharmacother.*, 56, pp. 388-396 (2002).

(Continued)

*Primary Examiner*—Lawrence E. Crane
(74) *Attorney, Agent, or Firm*—Bryan Cave LLP

(57) ABSTRACT

Compositions including, as the active ingredients, resveratrol, a derivative, metabolite or analogue thereof, and at least one additional component selected from epigallocatechin gallate (EGCG), genestein, vitamin E, polyunsaturated fatty acids, gamma-linolenic acid and vitamin K are disclosed. Also disclosed, are methods of making such compositions including admixing resveratrol, a derivative, metabolite or analogue thereof, and at least one additional component selected from EGCG, genestein, vitamin E, polyunsaturated fatty acids, gamma-linolenic acid and vitamin K are disclosed. Methods for the treatment or prevention of inflammatory diseases including administering to a subject in need of such treatment resveratrol, a derivative, metabolite or analogue thereof, in combination with at least one additional component selected from epigallocatechin gallate (EGCG), genestein, vitamin E, polyunsaturated fatty acids, gamma-linolenic acid and vitamin K are also disclosed.

4 Claims, No Drawings

OTHER PUBLICATIONS

Haqqi, T.M., et al., "Prevention of Collagen-Induced Arthritis in Mice by a Polyphenolic Fraction From Green Tea," *Immunology*, vol. 96, pp. 4524-4529 (1999).

Jang, M., et al., "Cancer Chemopreventive Activity of Resveratrol, a Natural Product Derived From Grapes," *Science*, vol. 275, pp. 218-220 (1997).

Murakami, A., et al., "Combinatorial Effects of Nonsteroidal Anti-inflammatory Drugs and Food Constituents on Production of Prostaglandin $E_2$ and Tumor Necrosis Factor-$\alpha$ in RAW264.7 Murine Macrophages," *Biosci. Biotechnol. Biochem.*, vol. 67, No. 5, pp. 1056-1062 (2003).

Murakami, A., et al., "Synergistic Suppression of Superoxide and Nitric Oxide Generation From Inflammatory Cells By Combined Food Factors," *Mutation Research*, Nos. 523-524, pp. 151-161 (2003).

Subbaramaiah, K., et al., "Resveratrol Inhibits Cyclooxygenase-2 Transcription and Activity in Phorbol Ester-treated Human Mammary Epithelial Cells," *J. Biol. Chem.*, vol. 273, No. 34, pp. 21875-21882 (1998).

Varilek, G.W., et al., "Green Tea Polyphenol Extract Attenuates Inflammation in Interleukin-2-Deficient Mice, a Model of Autoimmunity," *J. Nutr.*, 131, pp. 2034-2039 (2001).

Verdrengh, M., et al., "Genistein as an Anti-inflammatory Agent," *Inflamm. Res.*, 52, pp. 341-346 (2003).

Wolter, F. and Stein, J., "Biological Activities of Resveratrol and Its Analogs," *Drugs of the Future*, vol. 27, No. 10, pp. 949-959 (2002).

Derwent Database English language abstract of CN 1 127 070 A (B12 above), Abstract No. XP002295530.

\* cited by examiner

NUTRACEUTICAL COMPOSITIONS AND USE THEREOF

CROSS-REFERENCE TO RELATED APPLICATIONS

This application is the National Stage of International Application No. PCT/EP2004/005362, filed May 18, 2004.

The present invention relates to novel nutraceutical compositions comprising, as the active ingredients, resveratrol, a derivative, metabolite or analogue thereof, and at least one additional component selected from EGCG, genistein, vitamin E, polyunsaturated fatty acids, gamma-linolenic acid and vitamin K.

The term "nutraceutical" as used herein denotes a usefulness in both the nutritional and pharmaceutical field of application. Thus, the novel nutraceutical compositions can find use as supplement to food and beverages, and as pharmaceutical formulations for enteral or parenteral application which may be solid formulations such as capsules or tablets, or liquid formulations, such as solutions or suspensions. As will be evident from the foregoing, the term nutraceutical composition also comprises food and beverages containing the above-specified active ingredients.

The term "resveratrol, a derivative, metabolite or analogue thereof" as used herein comprises compounds encompassed by the general formula

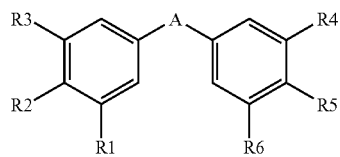

wherein A denotes a carbon-carbon double bond which may be trans or cis, and R1, R2, R3, R4, R5 and R6, independently denote hydrogen, hydroxy or etherified or esterified hydroxy groups. While the carbon-carbon double bond denoted by the symbol A may be trans or cis, formula I above is understood to also include cis/trans mixtures. However, compounds of formula I wherein A is a trans carbon-carbon bond are preferred.

Etherified or esterified hydroxy groups maybe derived from unsubstituted or substituted, straight or branched chain alkyl groups having 1 to 26 carbon atoms or from unsubstituted or substituted, straight or branched chain aliphatic, araliphatic or aromatic carboxylic acids having 1 to 26 carbon atoms. Etherified hydroxy groups may further be glycoside groups and esterified hydroxy groups may further be glucuronide or sulfate groups. Examples of compounds of formula I are resveratrol (R1, R3 and R5=hydrogen, R2, R4 and R6=hydroxy); piceatannol (R3 and R5=hydrogen, R1, R2, R4 and R6=hydroxy), and rhapontigenin (R5=hydrogen, R1, R3, R4 and R6=hydroxy, and R2=methoxy). Of primary interest for the purposes of the invention is (trans)-resveratrol.

The term "EGCG" as used herein comprises (−)-Epigallocatechin gallate and/or one or more derivatives (esterified forms, glycosides, sulphates) thereof.

The term "polyunsaturated fatty acids" as used herein (also referred to herein as PUFA) denotes a polyunsaturated fatty acid in an esterified (e.g., as triglycerides or ethyl esters) or a free form, particularly an omega-3 polyunsaturated fatty acid such as eicosapentaenoic acid (5,8,11,14,17-eicosapentaenoic acid, EPA) and docosahexaenoic acid (4,7,10,13,16,19-docosahexaenoic acid, DHA), or an omega-6-polyunsaturated fatty acid such as γ-linolenic acid (6,9,12-octadecatrienoic, GLA).

The term "vitamin K" as used herein comprises phylloquinone (vitamin $K_1$) and naphthoquinol and naphthoquinones having physiological properties similar to vitamin $K_1$, particularly vitamin $K_2$ and $K_3$.

The term "vitamin E" as used herein is a group of compounds based on 6-chromanol and includes racemic vitamin E (D,L-α-tocopherol) or natural vitamin E, as well as derivatives thereof which have biological vitamin E activity, e.g. other tocopherols or tocotrienols or carboxylic acid esters, such as vitamin E acetate, propionate, butyrate or succinate.

The term "genistein" as used herein comprises the aglycone (4',5, 7-trihydroxyisoflavone) and derivatives thereof, e.g., genistein glycosides, genistein sulfates, genistein glucuronides.

The active ingredients of the composition of this invention have different mechanism of action thus providing synergistic effects in the treatment or prevention of the diseases specified above, particularly inflammatory diseases.

Inflammatory disease are one of the most important health problems in the world. Inflammation is in general a localized protective response of the body tissues to invasion of the host by foreign material or injurious stimuli. The causes of inflammation are infectious agents such as bacteria, viruses, and parasites; physical agents such as burns or radiation; chemicals like toxins, drugs or industrial agents; and immunologic reactions such as allergies and autoimmune responses.

Two mains classes of drugs, the cortiocosteroid and the nonsteroidal anti-inflammatory drugs (NSAIDs) are used to treat inflammatory disorders. NSAIDs and corticosteroids provide essentially symptomatic relief. Corticosteroids use has declined due to a growing concern about the serious side effects of prolonged use. NSAIDs are among the most widely used drugs, primarily for the treatment of pain and inflammation, especially arthritis. However, chronic use of these drugs is also limited by their severe side-effects like serious gastrointestinal complications, renal toxicity or asthmatic reactions. Thus, there is a need for new anti-inflammatory agents with weak or no side effects. In view of the importance of inflammatory disease, in particular rheumatic disorders, there is a need for anti-inflammatory phytochemicals suitable for the treatment of non-acute rheumatoid symptoms. Patients with inflammatory diseases have a special interest in treatment considered as "natural" with mild anti-inflammatory effects and without major side effects, which can be used for disease prevention and as adjuvant treatment.

Inflammation is characterized by pain, redness, swelling, heat, and eventual loss of function of the affected area. These symptoms are the results of a complex series of interactions taking place between the cells of the immune system. The response of the cells results in an interacting network of three main families of inflammatory mediators: Proteins (e.g.,cytokines, enzymes (e.g., proteases, peroxydase), major basic protein (MPC), adhesion molecules (ICAM, VCAM), lipid mediators (e.g., eicosanoids, prostaglandins, leukotrienes, platelet activating factor (PAF)), reactive oxygen species (e.g.,hydroperoxides, superoxyde anion $O_2^-$, nitric oxide (NO). However, many of those mediators of inflammation are also regulators of normal cellular activity. Thus, deficiencies of inflammatory reactions lead to a compromised host (i.e. infection) while excessive inflammation leads to inflammatory diseases mediated in part by the over production of several of the above mentioned mediators. The treatment used need to maintain the equilibrium between excessive and insufficient inflammatory reaction.

Combination of natural products such as resveratrol and EGCG, genistein, vitamin E, omega-3 PUFA (e.g.,eicosapentaenoic acid, docosahexaenoic acid), borage oil (gamma-linolenic acid), vitamin K with mild anti-inflammatory activity and having different mechanism of action are very useful for maintaining such a balance.

Acute and chronic inflammation resulting form an excessive biosynthesis of inflammatory mediators is involved in numerous diseases such as arthritis (e.g., osteoarthritis, rheumatoid arthritis), asthma, inflammatory bowel diseases, inflammatory disease of the skin (e.g.,psoriasis, atopic dermatitis) and other chronic diseases with an inflammatory component such as atherosclerosis, heart diseases, diabetes, metabolic syndrome X, cancer, Alzheimer's disease and pre-stages thereof such as mild cognitive impairment.

Rheumatoid arthritis is a chronic inflammatory diseases of the joints. It is characterized by inflammation of the synovium and infiltration of the joints by neutrophils, macrophages and lymphocytes. As the disease progresses inflammation leads to synovial proliferation with damage to the articular cartilage and the bone underlying the cartilage with subsequent joint deformation and loss of function. Asthma and rheumatoid arthritis are characterised at the molecular level by chronically unbalanced expression of cytokines, chemokines, kinins and their receptors, adhesion molecules, and inflammatory enzymes such as inducible nitric oxide synthase (iNOS) and the inducible cyclooxygenase (COX-2). Proinflammatory cytokines play also a pivotal role in the development of osteoarthritis. Psoriasis is one of the most common skin problem, affecting 1-3% of the human population. Inflammatory bowel disease is a general term used to describe disease such as ulcerative colitis and Crohn's disease.

Atherosclerosis is currently considered as an inflammatory diseases of the vessel wall rather than simply a process of intravascular lipid deposition. Atherosclerosis results from vascular injury followed by an inflammation. Activated macrophages, T-lymphocytes, and mast cells are present in atherosclerotic plaques. Monocyte and lymphocyte activation leads to the release of eicosanoids and cytokines which are implicated in endothelial damage, as well as in the formation and eventually rupture of the atherosclerotic plaques. Finally, circulating inflammatory markers such as C-reactive protein (CRP), fibrinogen, and interleukins are increased in groups at high-risk of coronary artery diseases. Several clinical trials indicate that elevated CRP concentration correlates with increased risk of coronary, and vascular, events. Thus inflammation appears to play an important role in the initiation and progression of atheroma formation. Moreover, type 2 diabetes and obesity are risk factors for the development of coronary artery disease and atherosclerosis. Those conditions are associated with insulin resistance, oxidative stress, and inflammation.

A number of studies in animal models and humans indicate that inflammation, insulin insensitivity and disturbances in lipid metabolism are linked. Inflammatory mediators, such as plasma interleukin 6 (IL-6), tumor necrosis factor alpha (TNF-α) and CRP are elevated in type 2 diabetes and obesity. Adipose tissue can synthesize cytokines such as TNF-α and IL-6 which may promote inflammation in obesity. Therefore, anti-inflammatory agents may play a role not only in the prevention and treatment of atherosclerosis but also in diabetes and obesity.

Epidemiological studies showed a significant reduction in the risk of colorectal, gastric, esophageal, and breast cancers among people who take non-steroidal anti-inflammatory drugs (NSAIDs) compared with those not taking NSAIDs. In animal models NSAIDs significantly reduced tumor development. Increased levels of prostaglandins have been found in cancers of breast, colon, lung and pancreas in humans. Moreover, COX-2, is also overexpressed in a variety of tumors. Thus, COX inhibitors might be used in cancer prevention and treatment.

Inflammatory events are also associated with the pathophysiology of Alzheimer's disease. There is evidence of inflammation in the brain of patients with Alzheimer's disease. It is characterized by increased levels of cytokines and activated microglial cells. Epidemiological studies have suggested that patients taking NSAIDs have a lower risk of developing Alzheimer's disease than those not taking NSAIDs. A protective effect of NSAIDs suggests that the cyclooxygenases might be involved in the neurodegenerative process. Therefore, suppression of excessive production of inflammatory mediators may prevent and/or slow the progression of Alzheimer's disease.

Thus, inflammation is not only involved in the classical inflammatory diseases (e.g.,arthritis, asthma, bowel diseases) but is also associated with many chronic diseases (e.g.,atherosclerosis, heart diseases, diabetes, metabolic syndrome X, cancer, Alzheimer disease).

The compositions comprising a combination of active ingredients, i.e. resveratrol or derivatives and at least one additional component selected from EGCG, genistein, vitamin E, omega-3 PUFA (eicosapentaenoic acid, docosahexaenoic acid), borage oil (gamma-linolenic acid), and vitamin K are particularly useful for the treatment or prevention of disease with an inflammatory component. Moreover, a multi-vitamin and mineral supplement maybe added to the nutraceutical compositions of the present invention to obtain an adequate amount of an essential nutrient, which is missing in some diets. The multi-vitamin and mineral supplement may also be useful for disease prevention and protection against nutritional losses and deficiencies due to lifestyle patterns.

The nutraceutical compositions of the present invention contain resveratrol in an amount sufficient to administer to a human adult (weighing about 70 kg) a dosage from about 0.5 mg/day to about 2000 mg/day, preferably from about 5 mg/day to about 500 mg/day. Thus, if the nutraceutical composition is a food or beverage the amount of a resveratrol contained therein is suitably in the range from about 0.2 mg to about 500 mg per serving. If the nutraceutical composition is a pharmaceutical formulation such formulation may contain from about 0.5 mg to about 500 mg per solid dosage unit, e.g., per capsule or tablet, or from about 0.5 mg per daily dose to about 2000 mg per daily dose of a liquid formulation.

EGCG is preferably used in a concentration so that the daily consumption by a human adult (weighing about 70 kg) is in the range of from 10 mg/day to 2000 mg/day. A food or beverage suitably contains about 2 mg to about 500 mg of EGCG per serving. If the nutraceutical composition is a pharmaceutical formulation such formulation may contain a EGCG in an amount from about 5 mg to about 500 mg per dosage unit, e.g., per capsule or tablet, or from about 10 mg per daily dose to about 2000 mg per daily dose of a liquid formulation.

PUFA's are preferably used in a concentration so that the daily consumption by a human adult (weighing about 70 kg) is in the range of from 10 mg/day to 4000 mg/day. A food or beverage suitably contains about 5 mg to about 1000 mg of a PUFA per serving. If the nutraceutical composition is a pharmaceutical formulation such formulation may contain a PUFA in an amount from about 10 mg to about 1000 mg per dosage unit, e.g., per capsule or tablet, or from about 10 mg per daily dose to about 4000 mg per daily dose of a liquid formulation.

Genistein is preferably used in a concentration so that the daily consumption by a human adult (weighing about 70 kg) is in the range of from 0.5 mg/day to 2000 mg/day. A food or beverage suitably contains about 0.2 mg to about 500 mg of genistein per serving. If the nutraceutical composition is a pharmaceutical formulation such formulation may contain a genistein in an amount from about 0.5 mg to about 500 mg per dosage unit, e.g., per capsule or tablet, or from about 0.5 mg per daily dose to about 2000 mg per daily dose of a liquid formulation.

Vitamin E or its derivative is preferably used in a concentration so that the daily consumption by a human adult (weighing about 70 kg) is in the range of from 5 mg/day to 2000 mg/day. A food or beverage suitably contains about 2 mg to about 500 mg of vitamin E per serving. If the nutraceutical composition is a pharmaceutical formulation such formulation may contain vitamin E in an amount from about 5 mg to about 1000 mg per dosage unit, e.g., per capsule or tablet, or from about 5 mg per daily dose to about 2000 mg per daily dose of a liquid formulation.

Vitamin K is preferably used in a concentration so that the daily consumption by a human adult (weighing about 70 kg) is in the range of from 10 µg/day to 50 mg/day. A food or beverage suitably contains about 2 µg per serving to about 20 mg of vitamin K per serving. If the nutraceutical composition is a pharmaceutical formulation such formulation may contain a vitamin K in an amount from about 10 µg to about 25 mg per dosage unit, e.g., per capsule or tablet, or from about 10 µg per daily dose to about 50 mg per daily dose of a liquid formulation.

The term "serving" as used herein denotes an amount of food or beverage normally ingested by a human adult with a meal at a time and may range, e.g., from about 100 g to about 500 g.

In one aspect the present invention the compositions may be used as a nutritional supplement, e.g., as an additive to a multi-vitamin preparations comprising vitamins and minerals which are essential for the maintenance of normal metabolic function but are not synthesized in the body, especially for the treatment or prevention of inflammatory diseases.

According to another aspect of the invention the compositions maybe pharmaceutical compositions, preferably for enteral application, which may be solid or liquid galenical formulation. Examples of solid galenical formulations are tablets, capsules (e.g. hard or soft shell gelatin capsules), pills, sachets, powders, granules and the like which contain the active ingredient together with conventional galenical carriers. Any conventional carrier material can be utilized. The carrier material can be organic or inorganic inert carrier material suitable for oral administration. Suitable carriers include water, gelatin, gum arabic, lactose, starch, magnesium stearate, talc, vegetable oils, and the like. Additionally, additives such as flavouring agents, preservatives, stabilizers, emulsifying agents, buffers and the like maybe added in accordance with accepted practices of pharmaceutical compounding. While the individual active ingredients are suitably administered in a single composition they may also be administered in individual dosage units.

Specific combinations of active ingredients in the compositions of the present invention comprise
Resveratrol and EGCG;
Resveratrol and vitamin E;
Resveratrol and PUFA (EPA; DHA; GLA);
Resveratrol, vitamin E, EGCG;
Resveratrol, vitamin K, EGCG;
Resveratrol, vitamin E, PUFA (EPA; DHA; GLA);
Resveratrol, EGCG, vitamin E and PUFA (EPA; DHA; GLA);
Resveratrol, vitamin E, PUFA (EPA; DHA; GLA), genistein,
Resveratrol, EGCG, vitamin E, genistein, PUFA (EPA; DHA; GLA);

Most preferred are the combinations of resveratrol, EGCG, PUFA (EPA; DHA; GLA) with or without vitamin E; and resveratrol, EGCG, vitamin E, genistein, PUFA (EPA; DHA; GLA).

In order to determine anti-inflammatory properties of compounds or combinations thereof, appropriate cells or cell lines (i.e. whole blood, macrophages, leukocytes) will be activated with inflammatory stimuli in vitro in the presence of the compounds. This leads to the secretion of prostaglandins (i.e. the product of cyclooxygenase-2) and nitric oxide (synthesized by inducible nitric oxide synthase). Due to their anti-inflammatory effects, compounds will reduce the level of the two metabolites. Similarly, the expression of genes of inflammatory pathways will be monitored by quantitative PCR or by micro-array analysis. Anti-inflammatory compounds reduce their expression levels. Additive and/or synergistic effects of compounds will be identified both at the level of specific inflammatory parameters and more generally in the gene expression profile related to the cellular inflammatory response.

The antiinflammatory effect of a combined therapy with resveratrol and EGCG or EPA can be demonstrated in stimulated macrophages by determining the inhibition of the synthesis of nitric oxide and/or $PGE_2$.

In order to induce an in vitro 'inflammatory response', murine macrophages RAW264.7 were seeded into microtiter plates or 12- well plates and stimulated with lipopolysaccharide (LPS) without or with graded amounts of the test substances. Vehicle concentrations (i.e. DMSO) were kept constant. Culture supernatants were harvested after appropriate periods of time (4 to 24 hours). Prostaglandin $E_2$ ($PGE_2$) and nitrite produced from nitric oxide (NO) secreted into the culture medium were quantified by ELISA and the Griess reaction, respectively. The percentage of inhibition of $PGE_2$ or NO production at a given concentration of the test substances (compared to maximal production by LPS-stimulated cells) was calculated.

The results are indicated in Tables 1 and 2 below:

TABLE 1

Effects of Resveratrol and EGCG on the production of NO and $PGE_2$ in LPS-stimulated macrophages

| | % inhibition | |
|---|---|---|
| | NO | $PGE_2$ |
| Resveratrol (10 µM) | 8.3 | 26.8 |
| EGCG (10 µM) | 4.4 | 1.8 |
| Resveratrol (10 µM) + EGCG (10 µM) (calculated additive inhibition) | 12.7 | 28.6 |
| Resveratrol (10 µM) + EGCG (10 µM) (actually determined inhibition | 42.7 | 57.0 |

TABLE 2

Effects of Resveratrol and EPA on the NO production in LPS stimulated macrophages

|  | % inhibition NO |
|---|---|
| Resveratrol (2 μM) | 10.0 |
| EPA (12.5 μM) | 12.9 |
| Resveratrol (2 μM) + EPA (12.5 μM) (calculated additive inhibition) | 22.9 |
| Resveratrol (2 μM) + EPA (12.5 μM) (actually determined inhibition) | 34.1 |

The combined treatment with resveratrol and EGCG exerted a synergistic effect on NO and $PGE_2$ production in macrophages (Table 1). The combination of resveratrol and eicosapentaenoic Acid (EPA) had a synergistic effect on the production of NO by stimulated macrophages (Table 2). Thus, the data of Tables 1 and 2 show that combinations of resveratrol and EGCG and resveratrol and EPA exert a synergistic effect on the attenuation of the inflammatory response.

The following Examples illustrate the invention further.

A. Pharmaceutical Compositions May be Prepared by Conventional Formulation Procedures Using the Ingredients Specified Below:

EXAMPLE 1

Soft Gelatin Capsule
Soft gelatin capsules are prepared by conventional procedures using ingredients specified below:
Active ingredients: Resveratrol 10 mg, EPA 200 mg, vitamin E 50 mg
Other ingredients: glycerol, water, gelatine, vegetable oil

EXAMPLE 2

Hard Gelatin Capsule
Hard gelatin capsules are prepared by conventional procedures using ingredients specified below.
Active ingredients: resveratrol 10 mg, EGCG 100 mg, genistein, 5 mg, vitamin E 50 mg, vitamin K 1 mg
Other Ingredients:
Fillers: lactose or cellulose or cellulose derivatives q.s
Lubricant: magnesium sterate if necessary (0.5%)

EXAMPLE 3

Tablet
Tablets are prepared by conventional procedures using ingredients specified below:
Active ingredients: resveratrol 5 mg, EGCG 50 mg, vitamin E 20 mg
Other ingredients: microcrystalline cellulose, silicone dioxide ($SiO_2$), magnesium stearate, crosscarmellose sodium.

B. Food Items May be Prepared by Conventional Procedures Using Ingredients Specified Below.

EXAMPLE 4

Soft Drink with 30% Juice
Active Ingredients:
Resveratrol and one or more additional components selected from EGCG, PUFA (EPA; DHA; GLA), genistein, vitamin E and vitamin K are incorporated in this food item Resveratrol: 0.2-200 mg/per serving
EGCG: 2-200 mg/ per serving
PUFA (EPA; DHA, GLA): 5-500 mg/per serving
Genistein: 0.2-50 mg/ per serving
Vitamin E: 5-100 mg/ per serving
Vitamin K: 0.01-5 mg/ per serving
Typical serving: 240 ml I. A Soft Drink Compound is Prepared from the Following Ingredients:

| Juice concentrates and water soluble flavours | [g] |
|---|---|
| Orange concentrate |  |
| 60.3° Brix, 5.15% acidity | 657.99 |
| Lemon concentrate |  |
| 43.5° Brix, 32.7% acidity | 95.96 |
| Orange flavour, water soluble | 13.43 |
| Apricot flavour, water soluble | 6.71 |
| Water | 26.46 |
| 1.2 Color |  |
| β-Carotene 10% CWS | 0.89 |
| Water | 67.65 |
| 1.3 Acid and Antioxidant |  |
| Ascorbic acid | 4.11 |
| Citric acid anhydrous | 0.69 |
| Water | 43.18 |
| 1.4 Stabilizers |  |
| Pectin | 0.20 |
| Sodium benzoate | 2.74 |
| Water | 65.60 |
| 1.5 Oil soluble flavours |  |
| Orange flavour, oil soluble | 0.34 |
| Orange oil distilled | 0.34 |

1.6 Active Ingredients
Active ingredients (this means the active ingredient mentioned above: resveratrol and one or more of the following EGCG, PUFA (EPA; DHA; GLA), genistein, vitamin E and vitamin K) in the concentrations mentioned above Fruit juice concentrates and water soluble flavours are mixed without incorporation of air. The color is dissolved in deionized water. Ascorbic acid and citric acid is dissolved in water. Sodium benozoate is dissolved in water. The pectin is added unter stirring and dissolved while boiling. The solution is cooled down. Orange oil and oil soluble flavours are premixed. The active ingredients as mentioned under 1.6 are dry mixed and then stirred preferably into the fruit juice concentrate mixture (1.1).

In order to prepare the soft drink compound all parts 3.1.1 to 3.1.6 are mixed together before homogenising using a Turrax and then a high-pressure homogenizer ($p_1$=200 bar, $P_2$=50 bar).

II. A Bottling Syrup is Prepared from the Following Ingredients:

|  | [g] |
|---|---|
| Softdrink compound | 74.50 |
| Water | 50.00 |
| Sugar syrup 60° Brix | 150.00 |

The ingredients of the bottling syrup are mixed together. The bottling syrup is diluted with water to 1 l of ready to drink beverage.

Variations:

Instead of using sodium benzoate, the beverage may be pasteurised. The beverage may also be carbonised.

EXAMPLE 5

5 Cereal Bread
Active ingredients:
Resveratrol and one or more additional components selected from EGCG, PUFA (EPA; DHA; GLA), genistein, vitamin E and vitamin K are incorporated in this food item
Resveratrol: 0.2-100 mg/per serving
EGCG: 2-100 mg/per serving
PUFA (EPA; DHA, GLA): 5-200 mg/per serving
Genistein: 0.2-20 mg/per serving
Vitamin E: 5-100 mg/per serving
Vitamin K: 0.01-5 mg/per serving
Typical serving: 50 g

|  | [%] |
| --- | --- |
| 5 cereal flour | 56.8 |
| Water | 39.8 |
| Yeast | 2.3 |
| Salt | 1.1 |

The yeast is dissolved in a part of the water. All ingredients are mixed together to form a dough. Salt is added at the end of the kneading time. After fermentation, the dough is reworked and divided before a loaf is formed. Before baking, the surface of the loaf is brushed with water and sprinkled with flour.
Parameters:

| Kneading: | |
| --- | --- |
| Spiral kneading system | 4 min $1^{st}$ gear |
|  | 5 min $2^{nd}$ gear |
| Dough proofing: | 60 min |
| Dough temperature: | 22-24° C. |
| Proofing time: | 30 min |
| Baking: | |
| Oven: | Dutch type oven |
| Baking temperature: | 250/220° C. |
| Baking time: | 50-60 min |

EXAMPLE 6

Cookies Type Milano
Active ingredients:
Resveratrol and one or more additional components selected from EGCG, PUFA (EPA; DHA; GLA), genistein, vitamin E and vitamin K are incorporated in this food item
Resveratrol: 0.2-100 mg/per serving
EGCG: 2-100 mg/per serving
PUFA (EPA; DHA, GLA): 5-200 mg/per serving
Genistein: 0.2-20 mg/per serving
Vitamin E: 5-100 mg/per serving
Vitamin K: 0.01-5 mg/ per serving
Typical serving: 30 g

|  | [g] |
| --- | --- |
| Wheat Flour, type 550 | 41.0 |
| Sugar | 20.5 |
| Fat/Butter | 20.5 |
| Whole egg (liquid) | 18.0 |
| Lemon Flavour | q.s. |
| Baking agent | q.s. |

All ingredients are added slowly under mixing to form a sweet short pastry.

Afterwards, the pastry is kept cool (4° C.) for at least 2 hours before flattening the pastry to a thickness of approx. 5 mm. Pieces are cut out and brushed with egg yolk on the surface before baking.

Baking:

| Oven: | fan oven |
| --- | --- |
| Baking temperature: | 180° C. |
| Baking time: | 15 min |

EXAMPLE 7

Toast
Active ingredients:
Resveratrol and one or more additional components selected from EGCG, PUFA (EPA; DHA; GLA), genistein, vitamin E and vitamin K are incorporated in this food item
Resveratrol: 0.2-100 mg/per serving
EGCG: 2-100 mg/per serving
PUFA (EPA; DHA, GLA): 5-200 mg/per serving
Genistein: 0.2-20 mg/per serving
Vitamin E: 5-100 mg/per serving
Vitamin K: 0.01-5 mg/per serving
Typical serving: 100 g

|  | [%] |
| --- | --- |
| Wheat Flour, type 550 | 55.4 |
| Water | 33.2 |
| Yeast | 2.8 |
| Salt | 1.1 |
| Fat/Butter | 5.5 |
| Malt | 0.6 |
| Emulsifier baking agent | 1.4 |

The yeast is dissolved in a part of the water. All ingredients are mixed together to form a dough. Salt is added at the end of the kneading time. Afterwards, the dough is reworked, divided and placed in a baking tin for fermentation. After baking, the loaf is unmoulded directly.

Parameters:

| Kneading: | |
| --- | --- |
| Spiral kneading system | 5-6 min $1^{st}$ gear |
|  | 3-4 min $2^{nd}$ gear |
| Dough proofing: | none |

EXAMPLE 8

Yoghurt—Set Type
3.5% fat
Active ingredients:
Resveratrol and one or more additional components selected from EGCG, PUFA (EPA; DHA; GLA), genistein, vitamin E and vitamin K are incorporated in this food item
Resveratrol: 0.2-100 mg/per serving
EGCG: 2-100 mg/per serving
PUFA (EPA; DHA, GLA): 5-200 mg/per serving
Genistein: 0.2-20 mg/per serving
Vitamin E: 5-100 mg/per serving
Vitamin K: 0.01-5 mg/per serving
Typical serving: 225 g

|  | [%] |
|---|---|
| Full fat milk (3.8% fat) | 90.5 |
| Skimmed milk powder | 2.0 |
| Sugar | 5.0 |
| Culture | 2.5 |

The milk is heated to 35° C. before addition of milk powder, stabiliser, sugar and active ingredients. This mixture is heated to 65° C. to dissolve all ingredients. Then the mixture is homogenized in a high-pressure homogenizer ($p_1$=150 bar, $p_2$=50 bar) at 65° C. This emulsion is then pasteurised at 80° C. for 20 minutes. After cooling to 45° C. natural yoghurt/culture is added and mixed. Then this mixture is filled into cups and fermented at 45° C. for 3-4 hours until a pH of 4.3 is reached and then stored at 4° C.

EXAMPLE 9

Yoghurt—Stirred Type
3.5% fat
Resveratrol and one or more additional components selected from EGCG, PUFA (EPA; DHA; GLA), genistein, vitamin E and vitamin K are incorporated in this food item
Resveratrol: 0.2-100 mg/per serving
EGCG: 2-100 mg/per serving
PUFA (EPA; DHA, GLA): 5-200 mg/per serving
Genistein: 0.2-20 mg/per serving
Vitamin E: 5-100 mg/per serving
Vitamin K: 0.01-5 mg/per serving
Typical serving: 225 g

|  | [%] |
|---|---|
| Full fat milk (3.8% fat) | 90.2 |
| Skimmed milk powder | 2.0 |
| Stabiliser | 0.3 |
| Sugar | 5.0 |
| Culture | 2.5 |

The milk is heated to 35° C. before addition of milk powder, stabiliser, sugar and active ingredients. This mixture is heated to 65° C. to dissolve all ingredients before homogenisation in a high-pressure homogenizer ($p_1$=150 bar, $p_2$=50 bar) at 65° C. This emulsion is then pasteurised at 80° C. for 20 minutes. After cooling to 45° C. natural yoghurt/culture is added and mixed, followed by fermentation at 45° C. for 3-4 hours until a pH of 4.3 is reached. After cooling and stirring vigorously, the yoghurt is filled in cups and stored at 4° C.

EXAMPLE 10

Ice Cream
8% fat
Active ingredients:
Resveratrol and one or more additional components selected from EGCG, PUFA (EPA; DHA; GLA), genistein, vitamin E and vitamin K are incorporated in this food item
Resveratrol: 0.2-100 mg/per serving
EGCG: 2-100 mg/per serving
PUFA (EPA; DHA, GLA): 5-200 mg/per serving
Genistein: 0.2-20 mg/per serving
Vitamin E: 5-100 mg/per serving
Vitamin K: 0.01-5 mg/per serving
Typical serving: 85 g

|  | [g] |
|---|---|
| Milk (3.7% fat) | 600.00 |
| Cream (35% fat) | 166.00 |
| Skim milk powder | 49.10 |
| Sugar | 109.00 |
| Glucose syrup 80% | 70.00 |
| Ice cream stabiliser | 5.00 |
| Flavor | q.s. |
| Color | q.s |

Sugar, skim milk powder and stabiliser are added to the milk and cream, mixed and heated to 45° C. Then the colour as stock solution and the glucose syrup is added as well as the active ingredients. The mix is heated up and pasteurized (20 min, 80° C.). Then a homogenization step takes place. Afterwards the mix is cooled down under constant stirring and the flavour is added at 5° C. The mix maturated at 5° C. during at least 4 h and then passed through an the ice cream machine (overrun ca. 100%). The ice cream is filled into cups and stored at −20 to −30° C.

EXAMPLE 11

Wine Gums
Active ingredients:
Resveratrol and one or more additional components selected from EGCG, PUFA (EPA; DHA; GLA), genistein, vitamin E and vitamin K are incorporated in this food item
Resveratrol: 0.2-50 mg/per serving
EGCG: 2-50 mg/per serving -continued (Baking info from prior example:)
Dough temperature: 22-24° C.
Proofing time: 40 min
Baking:
Oven: Dutch type oven
Baking temperature: 220° C.
Baking time: 35-40 min PUFA (EPA; DHA, GLA): 5-100 mg/per serving
Genistein: 0.2-10 mg/per serving
Vitamin E: 5-10 mg/per serving
Vitamin K: 0.01-5 mg/per serving
Typical serving: 30 g

|  | [g] |
|---|---|
| Gelatine 200 Bloom | 80.0 |
| Water I | 125.0 |
| Sugar crys. | 290.0 |
| Water II | 120.0 |
| Glucose-syrup DE 38 | 390.0 |
| Citric acid | 10.0 |
| Flavour | 2.0 |
| Colour | q.s. |
| Yield ca | 1000.0 |

Disperse gelatine in water I, stir and dissolve by heating over a stream bath or using a microwave. Mix sugar with water II and bring to boiling until a clear solution is obtained. Remove from heat source. Mix with glucose syrup while dissolved sugar solution is still hot. Slowly add the gelatine solution. Let rest until foam on surface can be removed and 60-65° C. is reached. Add flavour, citric acid and the colour solution as well as active ingredients under stirring. Deposit into moulds printed into starch trays and let sit for at least 48 hours at RT. Remove starch powder and polish with oil or wax. Dry at RT and package into airtight pouch.

The invention claimed is:

1. A method for treating or reducing inflammation in a subject in need of such treatment which comprises administering to the subject a compound of formula I, in combination with (−)-epigallocatechin gallate (EGCG), wherein the compound of formula I is:

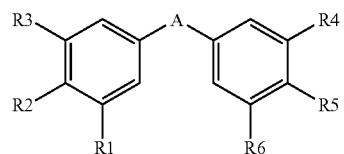

wherein A is a carbon-carbon double bond, and

R1, R2, R3, R4, R5 and R6 are independently selected from hydrogen, hydroxy, etherified hydroxy groups and esterified hydroxy groups;

a cis or trans isomer thereof, or a mixture of cis and trans isomers thereof.

2. The method of claim 1 wherein the compound of formula I is resveratrol.

3. The method of claim 2 wherein the resveratrol is administered in an amount of from about 0.5 mg/day to about 2000 mg/day and wherein the EGCG is in an amount of from about 10 mg/day to about 2000 mg/day.

4. The method of claim 2 wherein the resveratrol and the EGCG are administered in a unit dosage form of from about 0.5 mg to about 500 mg of resveratrol and from about 5 mg to about 500 mg EGCG.

* * * * *